United States Patent

Hamada et al.

[11] Patent Number: 5,716,722
[45] Date of Patent: Feb. 10, 1998

[54] ORGANIC ELECTROLLUMINESCENT DEVICE

[75] Inventors: Yuji Hamada, Kadoma; Takeshi Sano, Hirakata; Takanori Fujii, Sumoto; Kenichi Shibata, Hashimoto, all of Japan

[73] Assignee: Sanyo Electric Co., Ltd., Osaka, Japan

[21] Appl. No.: 588,816

[22] Filed: Jan. 19, 1996

[30] Foreign Application Priority Data

Jan. 28, 1995 [JP] Japan .................. 7-028740

[51] Int. Cl.$^6$ .................. B32B 9/00; H05B 33/12
[52] U.S. Cl. .................. 428/690; 428/704; 428/917; 428/457; 313/502; 313/504; 313/506
[58] Field of Search .................. 428/690, 704, 428/917, 457; 313/502, 504, 506

[56] References Cited

U.S. PATENT DOCUMENTS

| | | | |
|---|---|---|---|
| 5,077,142 | 12/1991 | Sakon et al. | 428/690 |
| 5,153,073 | 10/1992 | Ohnuma et al. | 428/461 |
| 5,346,772 | 9/1994 | Akiyama et al. | 428/457 |

*Primary Examiner*—Marie Yamnitzky
*Attorney, Agent, or Firm*—Armstrong, Westerman, Hattori, McLeland & Naughton

[57] ABSTRACT

In an organic electroluminescent device according to the present invention, at least a carrier transporting layer and a luminescent layer which use an organic material are provided between a hole injection electrode and an electron injection electrode, and at least one of a compound having a pyrimidine ring as its center skeleton and a compound having a triazine ring as its center skeleton is used for a hole transporting material in a hole transporting layer in the carrier transporting layer and the organic material in the luminescent layer.

9 Claims, 1 Drawing Sheet

ORGANIC ELECTROLUMINESCENT DEVICE

BACKGROUND OF THE INVENTION

1. Field of the Invention

The present invention relates generally to an organic electroluminescent device having at least a carrier transporting layer and a luminescent layer which use an organic material between a hole injection electrode and an electron injection electrode, and more particularly, to an organic electroluminescent device, in which an organic material used for a carrier transporting layer and a luminescent layer is hardly crystallized, capable of emitting light having stable, uniform and sufficient luminance.

2. Description of the Prior Art

In recent years, the needs of plane display devices the consumed power and the spatial occupied area of which are smaller than those of a CRT which has been conventionally generally employed have been increased as information equipments are diversified, for example, whereby an electroluminescent device (hereinafter referred to as an EL device) has been paid attention to as one of the plane display devices.

The EL device is roughly divided into an inorganic EL device using an inorganic material and an organic EL device using an organic material depending on the used material.

The inorganic EL device is so adapted that a high electric field is generally exerted on a luminescent portion, and electrons are accelerated within the high electric field to collide with a luminescence center, whereby the luminescence center is excited to emit light.

On the other hand, the organic EL device is so adapted that electrons and holes are respectively injected into a luminescent portion from an electron injection electrode and a hole injection electrode, the electrons and the holes thus injected are recombined with each other in a luminescence center to excite an organic material, and the organic material emits fluorescence when it is returned from its excited state to its ground state.

In the inorganic EL device, a high voltage of 100 to 200 V is required as its driving voltage because a high electric field is exerted as described above. On the other hand, the organic EL device can be driven at a low voltage of approximately 5 to 20 V.

Furthermore, in the organic EL device, a device for emitting light in a suitable color can be obtained by selecting a fluorescent material which is a luminescent material, whereby it is expected that the organic EL device can be utilized as a full-color display or the like. In recent years, therefore, various studies have been undertaken on the organic EL device.

Known examples of a device structure of the organic EL device include a three-layer structure which is referred to as a DH structure in which a hole transporting layer, a luminescent layer and an electron transporting layer are laminated between a hole injection electrode and an electron injection electrode, a two-layer structure which is referred to as an SH-A structure in which a hole transporting layer and a luminescent layer abundant in electron transporting characteristics are laminated between a hole injection electrode and an electron injection electrode, and a two-layer structure which is referred to as an SH-B structure in which a luminescent layer abundant in hole transporting characteristics and an electron transporting layer are laminated between a hole injection electrode and an electron injection electrode.

The organic EL device has the advantage that it can be driven at a lower voltage than the inorganic EL device so that it can be easily multi-colored. In the organic EL device, however, the stability of a hole transporting material in the hole transporting layer and a host material having hole transporting characteristics in the luminescent layer is not sufficient.

In the conventional organic EL device, therefore, the materials are gradually crystallized so that their crystals are deposited on the hole transporting layer and the luminescent layer, whereby a short circuit, for example, occurs within the organic EL device and light is not emitted in the portion. Consequently, it is impossible to stably emit light for a long time period, and it is difficult to obtain uniform and sufficient light emission as the entire organic EL device.

SUMMARY OF THE INVENTION

A first object of the present invention is to prevent a hole transporting material in a hole transporting layer and a host material having hole transporting characteristics in a luminescent layer from being crystallized to deposit crystals in the hole transporting layer and the luminescent layer.

Another object of the present invention is to provide an organic EL device capable of stably emitting light for a long time period.

Still another object of the present invention is to make it possible to emit light having uniform and sufficient luminance as the entire organic EL device.

In an organic EL device having at least a hole transporting layer and a luminescent layer which use an organic material between a hole injection electrode and an electron injection electrode, a first organic EL device according to the present invention is characterized in that at least one of a compound having a pyrimidine ring as its center skeleton and a compound having a triazine ring as its center skeleton is used for a hole transporting material in the hole transporting layer.

The first organic EL device should have a structure in which a hole transporting layer and a luminescent layer which use an organic material between a hole injection electrode and an electron injection electrode as described above. Its device structure may be either one of a DH structure and an SH-A structure as described above. The device structure is preferably the DH structure in order to increase luminous efficiency.

In an organic EL device having at least a carrier transporting layer and a luminescent layer which use an organic material between a hole injection electrode and an electron injection electrode, a second organic EL device is characterized in that at least one of a compound having a pyrimidine ring as its center skeleton and a compound having a triazine ring as its center skeleton is used for the organic material in the luminescent layer. In using the compound having a pyrimidine ring as its center skeleton and the compound having a triazine ring as its center skeleton for the organic material in the luminescent layer, the compounds are preferably used for a host material.

The second organic EL device should have a structure having a carrier transporting layer and a luminescent layer which use an organic material as described above. Its device structure may be any one of a DH structure, an SH-A structure, and an SH-B structure. The device structure is preferably the DH structure in order to increase luminous efficiency.

Furthermore, in each of the organic EL devices, a material having a large work function such as gold or ITO (indiumtin-oxide) is used as the hole injection electrode, while an electrode material having a small work function such as magnesium is used as the electron injection electrode. In order to take out EL light, at least one of the electrodes must be made transparent. In general, ITO which is transparent and has a large work function is used as the hole injection electrode.

Preferable examples of the hole transporting material used for the hole transporting layer in the first organic EL device and the host material used for the luminescent layer in the second organic EL device include compounds indicated by the following chemical formulas 1 to 4 each having a phenylamino group which is a functional group having hole transporting characteristics coupled to the pyrimidine ring used as a center skeleton and compounds indicated by the following chemical formulas 5 and 6 each having a phenylamino group which is a functional group having hole transporting characteristics coupled to the triazine ring used as a center skeleton:

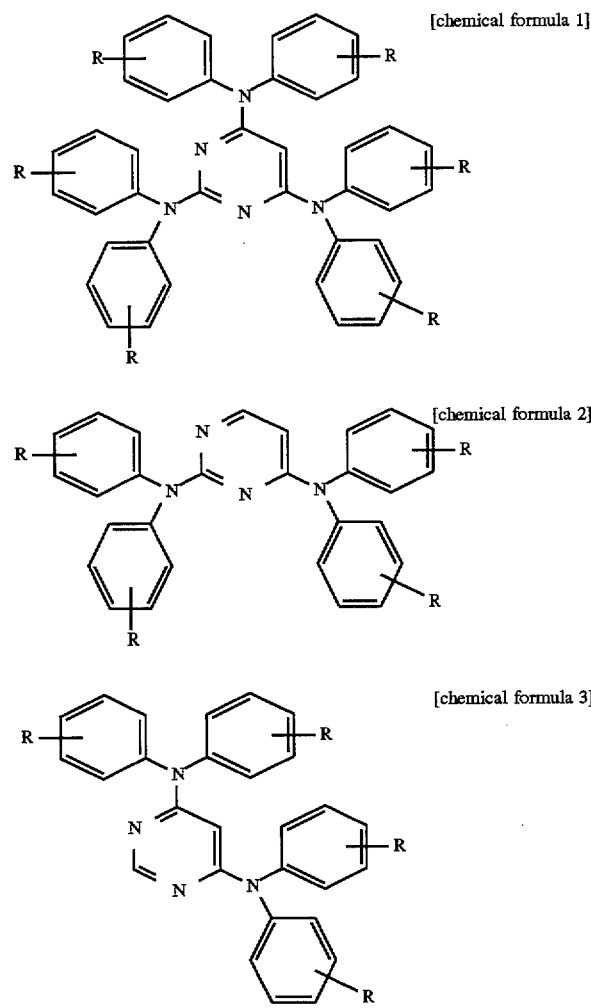

[chemical formula 1]

[chemical formula 2]

[chemical formula 3]

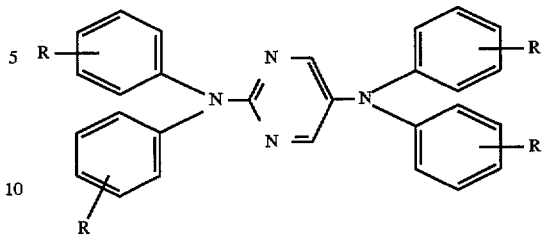

[chemical formula 4]

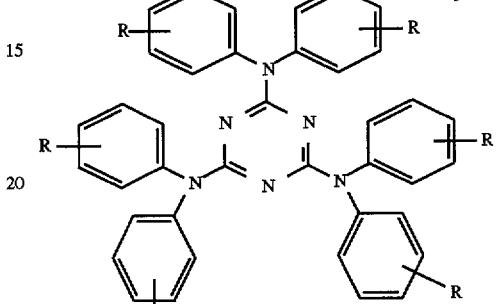

[chemical formula 5]

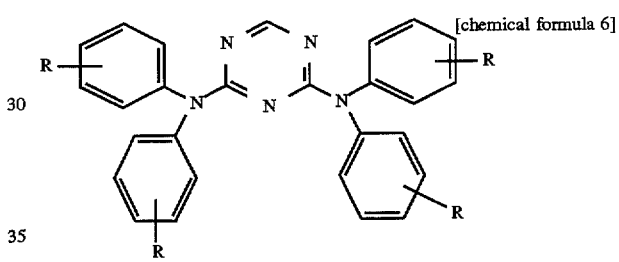

[chemical formula 6]

In the above-mentioned chemical formulas 1 to 6, R is composed of any one of substituting groups —$C_nH_{2n+1}$ (n is 0 to 10), —$OC_nH_{2n+1}$ (n is 0 to 5), $(C_nH_{2n+1})_2$ (n is 0 to 3), —Cl, —Br, —I, —CN, and —$NO_2$, and respective R may be the same or different from each other.

The compound having a pyrimidine ring as its center skeleton and the compound having a triazine ring as its center skeleton generally easily sublime when they are heated in a vacuum state. In fabricating the first and second organic EL devices, therefore, it is possible to simply form the hole transporting layer and the luminescent layer by evaporation or the like.

Furthermore, the compound having a pyrimidine ring as its center skeleton and the compound having a triazine ring as its center skeleton are generally difficult to crystallize. At the time of using the organic EL device, therefore, its crystals are prevented from being deposited in the hole transporting layer and the luminescent layer to cause a short circuit, for example. Therefore, light can be emitted uniformly and stably.

Additionally, when the compound having a phenylamino group which is a functional group having hole transporting characteristics is used as the compound having a pyrimidine ring as its center skeleton and the compound having a triazine ring as its center skeleton, hole transporting characteristics in the compounds are high. If such compounds are used for the organic material in the hole transporting layer and the host material in the luminescent layer, therefore, hole transporting characteristics in the hole transporting layer and the luminescent layer are improved, to improve luminous characteristics in the organic EL device.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Organic EL devices according to embodiments of the present invention will be specifically described on the basis of attached drawings and comparative examples will be taken, to clarify that the organic EL devices in the present embodiments are superior in durability or the like.

(Embodiment 1)

Figure 1:
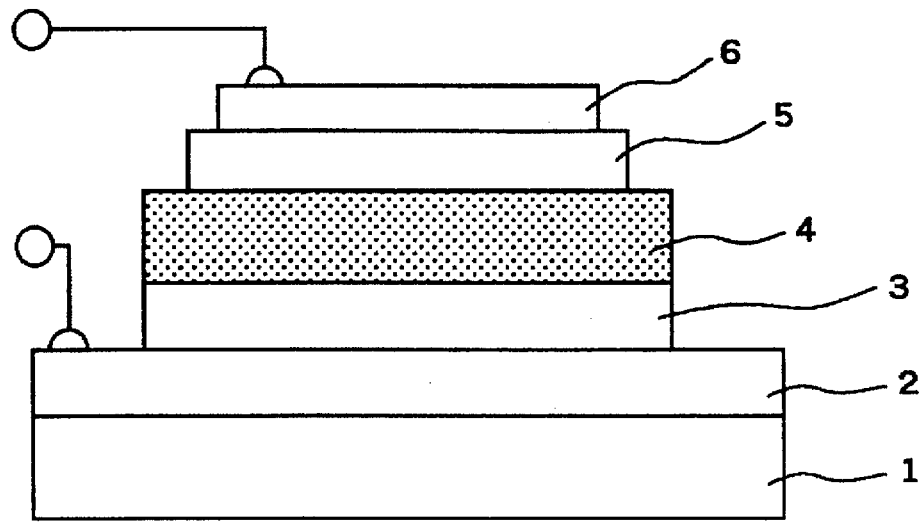
FIG. 1 is a schematic cross-sectional view showing an organic EL device having a DH structure.
Figure 2:
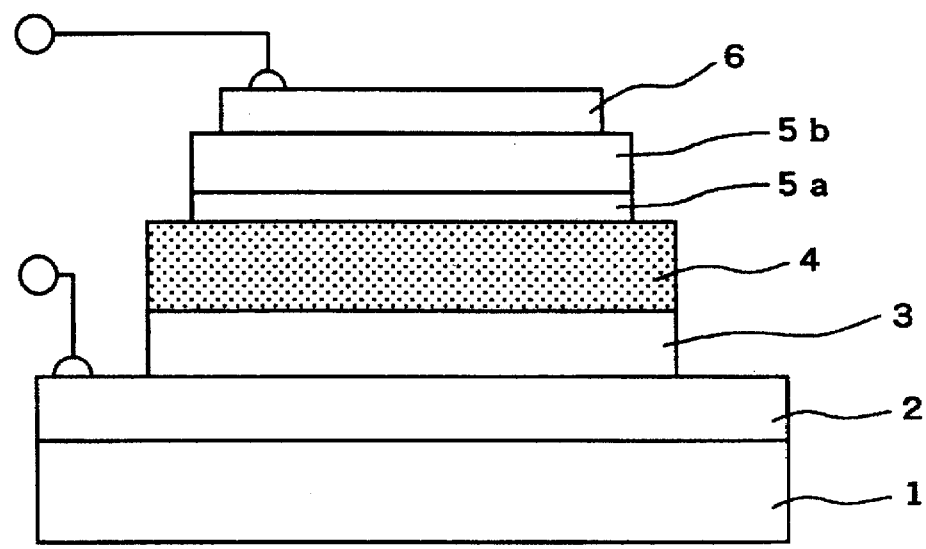
FIG. 2 is a schematic cross-sectional view showing an organic EL device according to an embodiment 5.

An organic EL device in the present embodiment has a DH structure in which a transparent hole injection electrode 2 composed of ITO, a hole transporting layer 3 having a thickness of 500 Å composed of m-MTDATA indicated by the following chemical formula 7 which is a triphenylamine derivative, a luminescent layer 4 having a thickness of 300 Å in which 5% by weight of a guest material composed of rubrene indicated by the following chemical formula 9 is doped into a host material composed of a pyrimidine derivative (hereinafter abbreviated as Me-PMD) having a pyrimidine ring as its center skeleton indicated by the following chemical formula 8, an electron transporting layer 5 having a thickness of 400 Å composed of (10-Hydroxybenzo[h]quinolinate)beryllium complex (hereinafter abbreviated as BeBq$_2$) indicated by the following chemical formula 10, and an electron injection electrode 6 having a thickness of 2000 Å composed of a magnesium-indium alloy (Mg: In=10:1) are successively formed on a glass substrate 1, as shown in FIG. 1.

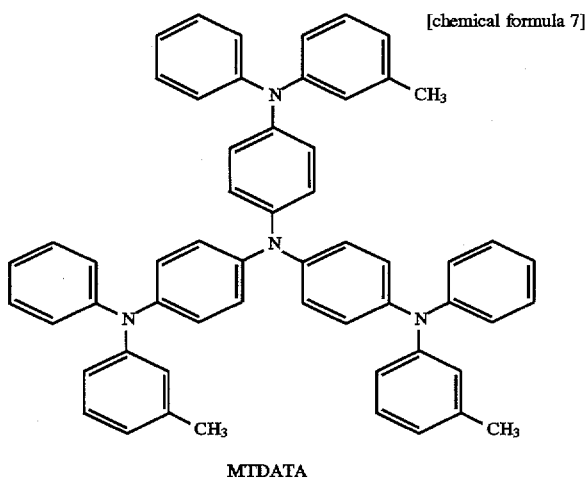

MTDATA

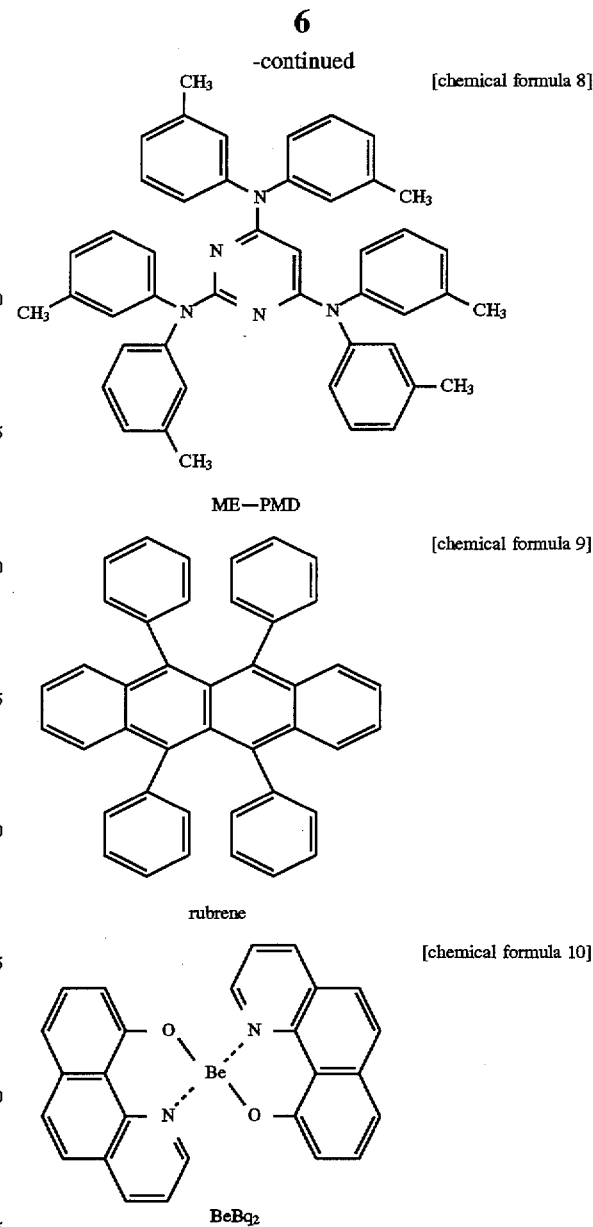

Description is now made of a method of synthesizing the Me-PMD having a pyrimidine ring as its center skeleton which is used for the host material in the luminescent layer 4.

1.06 g (8.5 mmol) of 2,4,6-triaminopyrimidine, 13.0 g (59.6 mmol) of 3-iodotoluene, 9.4 g (68 mmol) of anhydrous potassium carbonate, 0.54 g (8.5 mmol) of copper powder, and 40 ml of a nitrobenzene solvent were first put in a 200 ml eggplant type flask and was refluxed under an atmosphere of nitrogen for 19 hours, after which potassium carbonate, copper powder and the like in the solution were removed by suction filtration. Thereafter, nitrobenzene was removed from its filtrate under reduced pressure.

A solid residue which is left after thus removing nitrobenzene was purified by a sublimating and purifying apparatus using a train sublimation method (H. J. Wagner, R. O. Loutfy, and C. K. Hisao; J. Mater. Sci. Vol. 17, P2781 (1982)), an obtained solid was further passed through a silica gel column using toluene as a developing solvent to obtain a toluene solution, and the toluene solution was condensed, after which a deposited solid was then gathered, and was recrystallized and purified using a solvent of hexane:toluene=6:1.

The Me-PMD thus synthesized was elementally analyzed, to exhibit calculated values and actual values.

Elemental analysis; calculated values H (6.51), C (82.97), N (10.52) actual values H (6.59), C (82.83), N (10.48)

As a result, in the Me-PMD synthesized in the above-mentioned manner, the actual values of H, C and N almost coincide with their calculated values. In addition, the fluorescent peak wavelength of the Me-PMD is 376 nm.

Description is now made of a method of fabricating an organic EL device according to the present embodiment.

First, a glass substrate 1 having a hole injection electrode 2 composed of ITO on its surface was cleaned by a neutral detergent, and was then ultrasonically cleaned in acetone for twenty minutes and in ethanol for twenty minutes. The glass substrate 1 was put in boiled ethanol for approximately one minute and was taken out, after which the glass substrate 1 was dried by ventilation. Thereafter, the above-mentioned MTDATA was vacuum evaporated on the hole injection electrode 2, to form a hole transporting layer 3. The above-mentioned Me-PMD and rubrene were co-evaporated on the hole transporting layer 3 to form a luminescent layer 4, after which the above-mentioned BeBq$_2$ was vacuum evaporated on the hole transporting layer 3 to form an electron transporting layer 5, and an electron injection electrode 6 composed of a magnesium-indium alloy was formed by vacuum evaporation on the electron transporting layer 5. The evaporation was performed at a degree of vacuum of $1 \times 10^{-6}$ Torr, and the substrate temperature was not particularly controlled.

When a positive voltage and a negative voltage are respectively applied to the hole injection electrode 6 and the electron injection electrode 2 in the organic EL device according to the present embodiment, high-luminance yellow light the maximum luminance of which is 14500 cd/m$^2$ (having a peak wavelength of 560 nm) could be obtained at a voltage of 14 V and a current density of 340 mA/cm$^2$.

(Embodiment 2)

An organic EL device according to the present embodiment also has the same DH structure as that of the organic EL device according to the above-mentioned embodiment 1. The organic EL device in the present embodiment is obtained in the same manner as that in the first embodiment 1 except that the above-mentioned Me-PMD is used for a hole transporting material in a hole transporting layer 3, tBu-TPD indicated by the following chemical formula 11 and the above-mentioned rubrene are respectively used for a host material and a guest material in a luminescent layer 4 and are co-evaporated to form a luminescent layer 4 in which 5% by weight of the guest material composed of the rubrene is doped into the host material composed of the tBu-TPD.

[chemical formula 11]

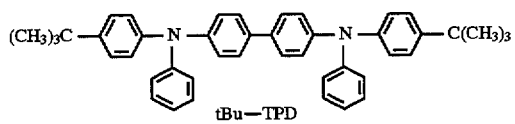

tBu—TPD

When a positive voltage and a negative voltage are respectively applied to a hole injection electrode 6 and an electron injection electrode 2 in the organic EL device according to the present embodiment, high-luminance yellow light the maximum luminance of which is 1400 cd/m$^2$ (having a peak wavelength of 560 nm) could be obtained at a voltage of 28 V and a current density of 25 mA/cm$^2$.

(Embodiment 3)

An organic EL device according to the present embodiment also has the same DH structure as that of the organic EL device according to the above-mentioned embodiment 1. The organic EL device in the present embodiment is obtained in the same manner as that in the embodiment 1 except that a triazine derivative (hereinafter abbreviated as Me-TAZ) having a triazine ring as its center skeleton indicated by the following chemical formula 12 and the above-mentioned rubrene are respectively used for a host material and a guest material in a luminescent layer 4 and are co-evaporated to form a luminescent layer 4 in which 5% by weight of the guest material composed of the rubrene is doped into the host material composed of the Me-TAZ.

[chemical formula 12]

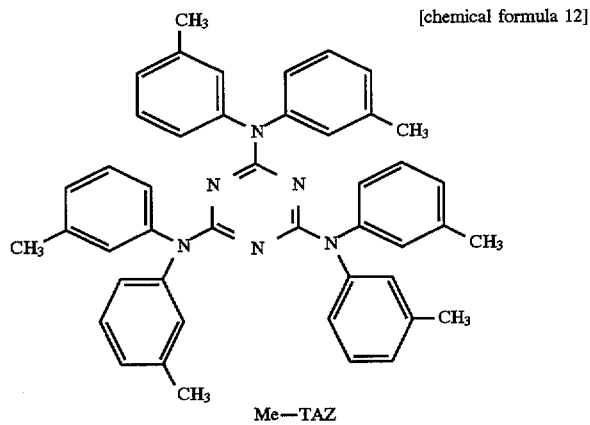

Me—TAZ

Description is now made of a method of synthesizing the above-mentioned Me-TAZ having a triazine ring which is used for the host material in the luminescent layer 4.

1.07 g (8.5 mmol) of melamine, 13.0 g (59.6 mmol) of 3-iodotoluene, 9.4 g (68 mmol) of anhydrous potassium carbonate, 0.54 g (8.5 mmol) of copper powder, and 40 ml of a nitrobenzene solvent were first put in a 200 ml eggplant type flask and was refluxed under an atmosphere of nitrogen for 30 hours, after which potassium carbonate, copper powder, and the like in the above-mentioned solution were removed by suction filtration. Thereafter, nitrobenzene was removed from its filtrate under reduced pressure.

A solid residue which is left after thus removing nitrobenzene was purified by a sublimating and purifying apparatus using a train sublimation method, an obtained solid was further passed through a silica gel column using toluene as a developing solvent to obtain a toluene solution, and the toluene solution was condensed, after which the deposited solid was gathered, and was further recrystallized and purified using hexane.

Examples of the Me-TAZ thus synthesized is elementally analyzed, to exhibit calculated values and actual values.

Elemental analysis; calculated values H (6.35), C (81.05), N (12.60) actual values H (6.87), C (81.28), N (12.71)

As a result, in Me-PMD synthesized in the above described manner, the actual values of H, C and N almost coincide with their calculated values. In addition, the fluorescent peak wavelength of the Me-TAZ is 370 nm.

When a positive voltage and a negative voltage are respectively applied to a hole injection electrode 6 and an electron injection electrode 2 in the organic EL device according to the present embodiment, high-luminance yellow light the maximum luminance of which is 10200 cd/m$^2$ (having a peak wavelength of 560 nm) could be obtained at a voltage of 15 V and a current density of 220 mA/cm$^2$.

(Embodiment 4)

An organic EL device according to the present embodiment also has the same DH structure as that of the organic EL device according to the above-mentioned embodiment 1. The organic EL device according to the present embodiment is obtained in the same manner as that in the embodiment 1 except that the above-mentioned Me-TAZ is used for a hole transporting material in a hole transporting layer 3, the above-mentioned tBu-TPD and rubrene are respectively used for a host material and a guest material in a luminescent layer 4 and are co-evaporated to form a luminescent layer 4 in which 5% by weight of the guest material composed of the rubrene is doped into the host material composed of the tBu-TPD.

When a positive voltage and negative voltage are respectively applied to a hole injection electrode 6 and an electron injection electrode 2 in the organic EL device according to the present embodiment, high-luminance yellow light the maximum luminance of which is 1000 cd/m$^2$ (having a peak wavelength of 560 nm) could be obtained at a voltage of 29 V and a current density of 23 mA/cm$^2$.

(Comparative example 1)

An organic EL device in the comparative example has the same DH structure as that of the organic EL device according to the above-mentioned embodiment 1. The organic EL device is obtained in the same manner as that in the embodiment 1 except that a known oxadiazole derivative (hereinafter abbreviated as NEt-OXD) indicated by the following chemical formula 13 is used for a hole transporting material in a hole transporting layer 3, the above-mentioned tBu-TPD and rubrene are respectively used for a host material and a guest material in a luminescent layer 4 and are co-evaporated to form a luminescent layer 4 in which 5% by weight of the guest material composed of the rubrene is doped into the host material composed of the tBu-TPD.

[chemical formula 13]

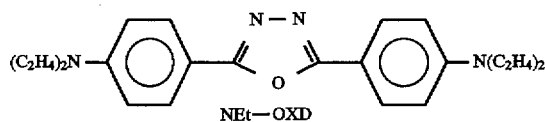

NEt—OXD

When a positive voltage and a negative voltage are respectively applied to a hole injection electrode 6 and an electron injection electrode 2 in the organic EL device in this comparative example, high-luminance yellow light the maximum luminance of which is 200 cd/m$^2$ (having a peak wavelength of 560 nm) could be obtained at a voltage of 25 V and a current density of 20 mA/cm$^2$.

(Comparative example 2)

An organic EL device in the comparative example also has the same DH structure as that of the organic EL device according to the above-mentioned embodiment 1. The organic EL device is obtained in the same manner as that in the above-mentioned embodiment 1 except that the above-mentioned NEt-OXD and rubrene are respectively used for a host material and a guest material in a luminescent layer 4 and are co-evaporated to form a luminescent layer 4 in which 5% by weight of the guest material composed of the rubrene is doped into the host material composed of the NEt-OXD.

When a positive voltage and a negative voltage are respectively applied to a hole injection electrode 6 and an electron injection electrode 2 in the organic EL device in this comparative example, high-luminance yellow light the maximum luminance of which is 3000 cd/m$^2$ (having a peak wavelength of 560 nm) could be obtained at a voltage of 23 V and a current density of 200 mA/cm$^2$.

With respect to the respective EL devices in the above-mentioned embodiments 1 to 4 and comparative examples 1 and 2, durability and self stability are then examined. With respect to the durability and the self stability, each of the organic EL devices was preserved in dry air and was periodically energized, to find the number of days on which light is emitted by the energization. The results thereof are indicated by the following Table 1.

TABLE 1

|  | embodiment | | | | comparative example | |
|---|---|---|---|---|---|---|
|  | 1 | 2 | 3 | 4 | 1 | 2 |
| the number of days on which light is emitted | 50 | 43 | 35 | 30 | 5 | 5 |

As a result, the number of days on which light is emitted in the organic EL device according to each of the embodiments is significantly larger than that in the organic EL device in each of the comparative examples 1 and 2, whereby durability and preservation are improved.

The states of the organic EL devices in the comparative examples were observed using a light microscope. In each of the organic EL devices, crystals which are considered to be the above-mentioned NEt-OXD are deposited, whereby it is found that the device structure of the organic EL device is destroyed. Further, even when only NEt-OXD is evaporated on the glass substrate, it is confirmed that crystals are similarly deposited in five days.

Although in each of the above-mentioned embodiments, description was made of the organic EL device having a DH structure, the organic EL device can have an SH-A structure in a case where a compound having a pyrimidine ring or a triazine ring as its center skeleton is used for a hole transporting layer, and can have either one of an SH-A structure and an SH-B structure in a case where the above-mentioned compound is used for a host material in a luminescent layer.

(Embodiment 5)

In an organic EL device in the present embodiment, a hole transporting layer 3 having a thickness of 300 Å is formed on a transparent hole injection electrode 2 formed using ITO on a glass substrate 1 using tBu-TPD indicated by the foregoing chemical formula 11, and a luminescent layer 4 having a thickness of 300 Å is formed on the hole transporting layer 3 using the above-mentioned Me-PMD having a pyrimidine ring as its center skeleton, after which a second electron transporting layer 5a having a thickness of 100 Å is formed using a triazole derivative (TAZ) indicated by the following chemical formula 14 on the luminescent layer 4, and a first electron transporting layer 5b having a thickness of 400 Å is formed on the second electron transporting layer 5a using BeBq$_2$ indicated by the following chemical formula 10, and an electron injection electrode 6 composed of a magnesium-indium alloy is further formed on the first electrode transporting layer 5b.

[chemical formula 14]

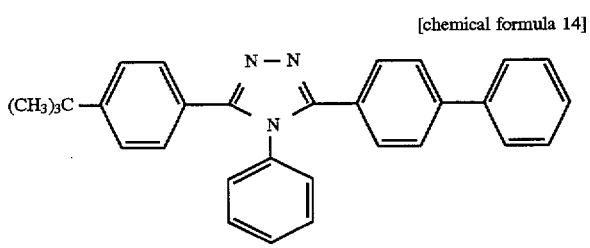

TAZ

When a positive voltage and a negative voltage are respectively applied to the hole injection electrode 6 and the electron injection electrode 2 in the organic EL device according to the present embodiment, Me-PMD used for the luminescent layer 4 emits light, whereby blue light having luminance of 700 cd/m² is obtained at a voltage of 15 V and a current density of 200 mA/cm².

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An organic electroluminescent device having at least a hole transporting layer and a luminescent layer which use an organic material between a hole injection electrode and an electron injection electrode, wherein a compound having a triazine ring with at least one diphenylamino group directly attached thereto is used for a hole transporting material in the hole transporting layer.

2. The organic electroluminescent device according to claim 1, wherein at least one of compounds indicated by the following chemical formulas 5 and 6 is used for the hole transporting material in the hole transporting layer,

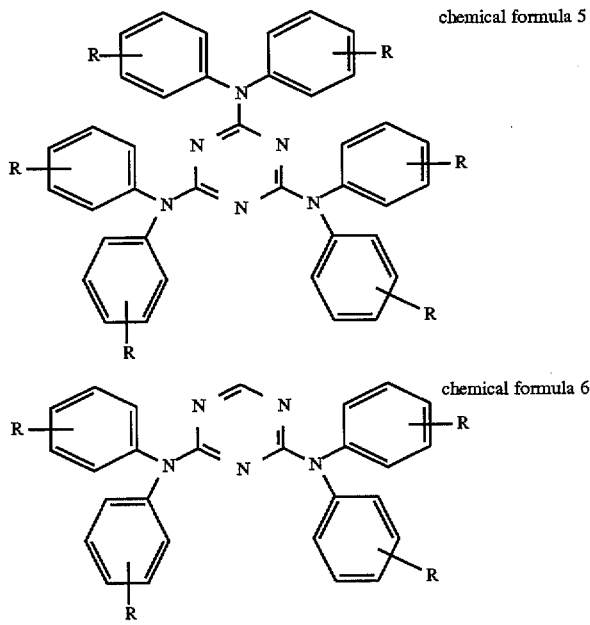

chemical formula 5 chemical formula 6 where R is any one of —$C_nH_{2n+1}$ (n is 0 to 10), —$OC_nH_{2n+1}$ (n is 0 to 5), —N $(C_nH_{2n+1})_2$ (n is 0 to 3), —Cl, —Br, —I, —CN, and —$NO_2$, and respective R's may be the same or different from each other.

3. An organic electroluminescent device having at least a carrier transporting layer and a luminescent layer which use an organic material between a hole injection electrode and an electron injection electrode, wherein a compound having a triazine ring with at least one diphenylamino group directly attached thereto is used for the organic material in said luminescent layer.

4. The organic electroluminescent device according to claim 3, wherein a hole transporting layer, a luminescent layer and an electron transporting layer which use an organic material are provided between the hole injection electrode and the electron injection electrode.

5. The organic electroluminescent device according to claim 3, wherein at least one of compounds indicated by the following chemical formulas 5 and 6 is used for the organic material in said luminescent layer,

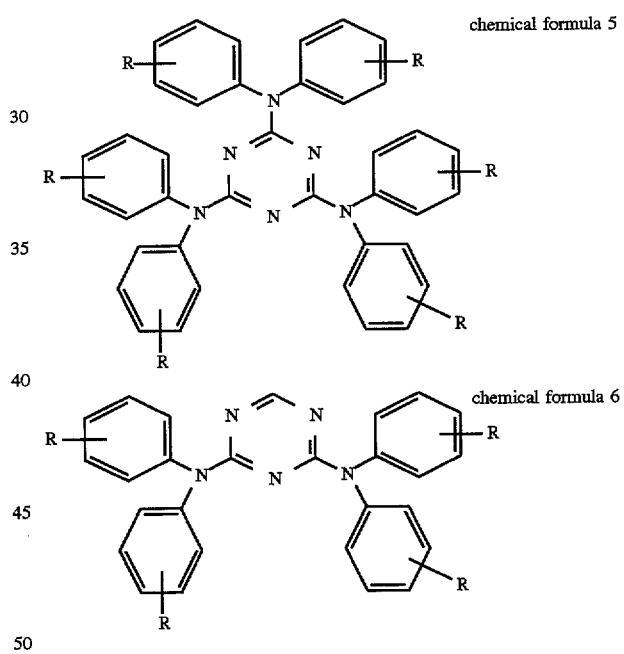

chemical formula 5 chemical formula 6 where R is any one of —$C_nH_{2n+1}$ (n is 0 to 10), —$OC_nH_{2n+1}$ (n is 0 to 5), —N$(C_nH_{2n+1})_2$ (n is 0 to 3), —Cl, —Br, —I, —CN, and —$NO_2$, and respective R's may be the same or different from each other.

6. An organic electroluminescent device having at least a hole transporting layer and a luminescent layer which use an organic material between a hole injection electrode and an electron injection electrode, wherein at least one of compounds indicated by the following chemical formulas 1 to 4 is used for the hole transporting material in the hole transporting layer, chemical formula 1

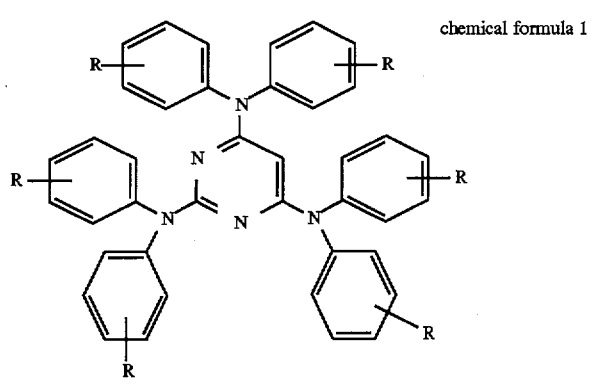

chemical formula 1

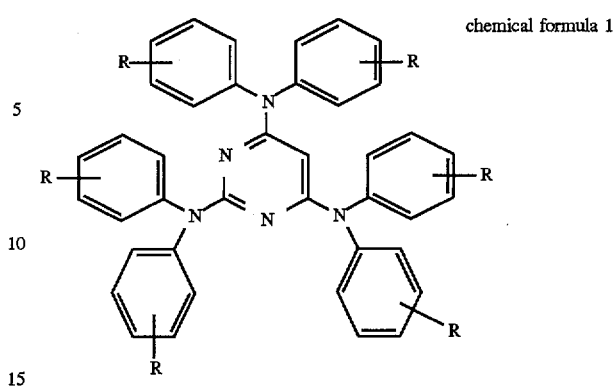

chemical formula 2

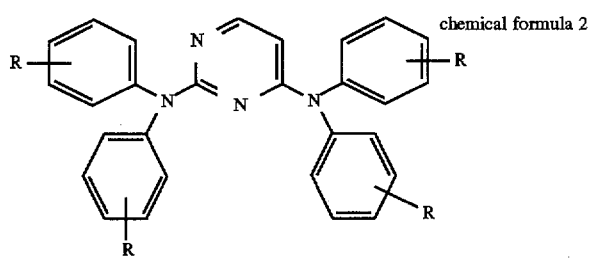

chemical formula 2

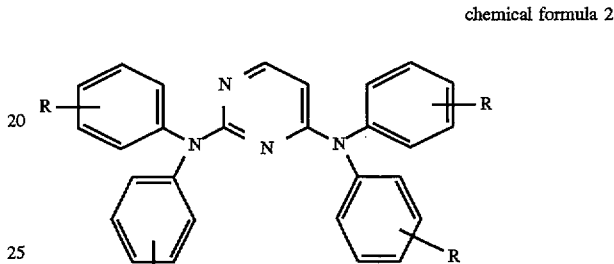

chemical formula 3

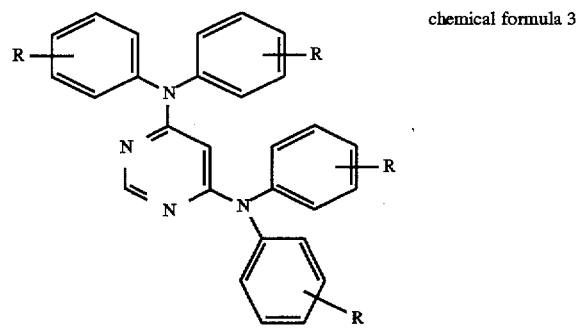

chemical formula 3

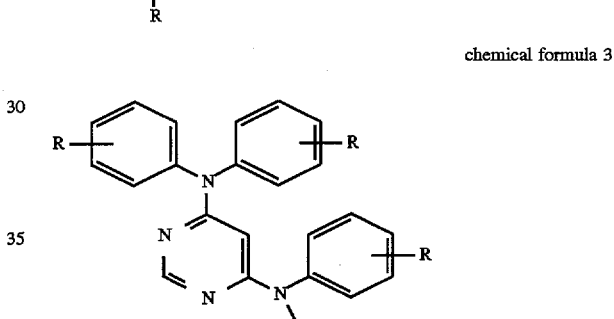

chemical formula 4

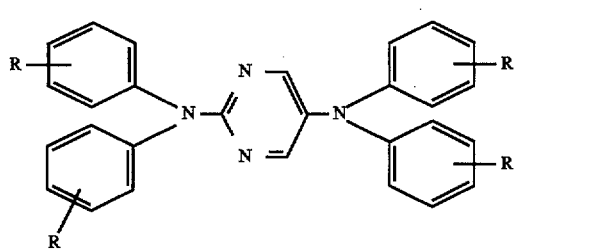

chemical formula 4

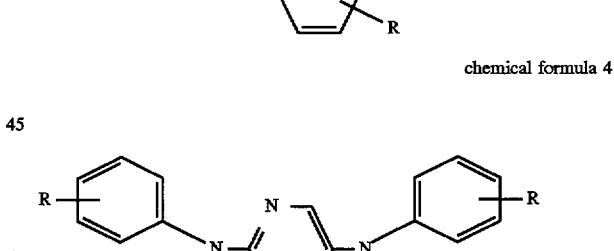

where R is any one of —$C_nH_{2n+1}$ (n is 0 to 10), —$OC_nH_{2n+1}$ (n is 0 to 5), —$N(C_nH_{2n+1})_2$ (n is 0 to 3), —Cl, —Br, —I, —CN, and —$NO_2$, and respective R's may be the same or different from each other.

7. An organic electroluminescent device having at least a carrier transporting layer and a luminescent layer which use an organic material between a hole injection electrode and an electron injection electrode, wherein at least one of compounds indicated by the following chemical formulas 1 to 4 is used for the organic material in said luminescent layer, where R is any one of —$C_nH_{2n+1}$ (n is 0 to 10), —$OC_nH_{2n+1}$ (n is 0 to 5), —$N(C_nH_{2n+1})_2$ (n is 0 to 3), —Cl, —Br, —I, —CN, and —$NO_2$, and respective R's may be the same or different from each other.

8. The organic electroluminescent device having at least a carrier transporting layer and a luminescent layer which use an organic material between a hole injection electrode and an electron injection electrode, wherein at least one of a compound having a pyrimidine ring with at least one diphenylamino group directly attached thereto or a compound having a triazine ring with at least one diphenylamino group directly attached thereto is used for the organic material in said luminescent layer, said luminescent layer has a host material and a guest material, and at least one of said compound having a pyrimidine ring and said compound having a triazine ring is used for the host material.

9. The organic electroluminescent device according to claim 8, wherein rubrene is used for said guest material in the luminescent layer.

* * * * *